US009820697B2

(12) United States Patent
Takata et al.

(10) Patent No.: US 9,820,697 B2
(45) Date of Patent: Nov. 21, 2017

(54) LESION DETERMINATION APPARATUS, SIMILAR CASE SEARCHING APPARATUS, LESION DETERMINATION METHOD, SIMILAR CASE SEARCHING METHOD, AND NON-TRANSITORY COMPUTER-READABLE STORAGE MEDIUM

(71) Applicant: Panasonic Corporation, Osaka (JP)

(72) Inventors: Kazutoyo Takata, Fukui (JP); Kazuki Kozuka, Fukui (JP); Kenji Kondo, Fukui (JP); Hirohiko Kimura, Fukui (JP); Toyohiko Sakai, Fukui (JP)

(73) Assignee: PANASONIC CORPORATION, Osaka (JP)

( * ) Notice: Subject to any disclaimer, the term of this patent is extended or adjusted under 35 U.S.C. 154(b) by 465 days.

(21) Appl. No.: 14/642,762

(22) Filed: Mar. 10, 2015

(65) Prior Publication Data
US 2015/0173684 A1 Jun. 25, 2015

Related U.S. Application Data

(63) Continuation of application No. PCT/JP2014/003236, filed on Jun. 17, 2014.

(30) Foreign Application Priority Data

Aug. 1, 2013 (JP) .................................. 2013-160366

(51) Int. Cl.
*G06K 9/00* (2006.01)
*A61B 5/00* (2006.01)
(Continued)

(52) U.S. Cl.
CPC ............ *A61B 5/7246* (2013.01); *A61B 5/055* (2013.01); *A61B 5/08* (2013.01); *A61B 5/7282* (2013.01);
(Continued)

(58) Field of Classification Search
CPC ......... A61B 5/7246; A61B 5/055; A61B 5/08; A61B 5/7282; A61B 5/748; A61B 6/032;
(Continued)

(56) References Cited

U.S. PATENT DOCUMENTS

| 2008/0151187 | A1* | 6/2008 | Tsukada | ............ | G01N 21/4795 351/206 |
| 2010/0280364 | A1* | 11/2010 | Lu | .......................... | A61B 5/055 600/424 |
| 2012/0065494 | A1* | 3/2012 | Gertner | .................. | A61B 5/055 600/411 |

FOREIGN PATENT DOCUMENTS

| JP | 2002-253545 | 9/2002 |
| JP | 2007-260064 | 10/2007 |

(Continued)

OTHER PUBLICATIONS

Bigler, Erin D. "The lesion (s) in traumatic brain injury: Implications for clinical neuropsychology." Archives of clinical neuropsychology 16.2 (2001): 95-131.*

(Continued)

*Primary Examiner* — Shefali Goradia
(74) *Attorney, Agent, or Firm* — Wenderoth, Lind & Ponack, L.L.P.

(57) ABSTRACT

A lesion determination apparatus includes: a number-of-images acquiring unit configured to acquire and record, on occurrence of a direction change that is either a first state in which a second operation instruction is received immediately after receipt of a first operation instruction or a second state in which the first operation instruction is received immediately after a receipt of the second operation instruction, a number of one-directionally viewed images that is either a number of tomography images continuously viewed in response to continuous first operation instructions including the first operation instruction in the first state or a (Continued)

number of tomography images continuously viewed in response to continuous second operation instructions including the second operation instruction in the second state; and a locality determining unit configured to determine whether the object part is a focal lesion or a diffuse lesion based on a change in the number of one-directionally viewed images.

17 Claims, 15 Drawing Sheets

(51) Int. Cl.

| | | |
|---|---|---|
| A61B 5/055 | (2006.01) | |
| A61B 5/08 | (2006.01) | |
| A61B 6/00 | (2006.01) | |
| A61B 6/03 | (2006.01) | |
| A61B 8/13 | (2006.01) | |
| A61B 8/08 | (2006.01) | |
| G06F 19/00 | (2011.01) | |

(52) U.S. Cl.
CPC ............... *A61B 5/748* (2013.01); *A61B 6/032* (2013.01); *A61B 6/5217* (2013.01); *A61B 8/13* (2013.01); *A61B 8/5223* (2013.01); *A61B 2576/02* (2013.01); *G06F 19/321* (2013.01); *G06F 19/3443* (2013.01)

(58) Field of Classification Search
CPC ....... A61B 6/5217; A61B 8/13; A61B 8/5223; A61B 2576/02; G06F 19/321; G06F 19/3443
See application file for complete search history.

(56) References Cited

FOREIGN PATENT DOCUMENTS

| | | |
|---|---|---|
| JP | 2007-275216 | 10/2007 |
| JP | 2010-000130 | 1/2010 |

OTHER PUBLICATIONS

International Search Report of PCT application No. PCT/JP2014/003236 dated Sep. 2, 2014.

Mitsutaka Nemoto et al., "Improvement of Tumor Detection Performance in Mammograms by Feature Selection from a Large Number of Features and Proposal of Fast Feature Selection Method" D-II vol. J88-D-II, No. 2, IEICE, 2005, pp. 416-426 (Partial Translation).

Ryosuke Urayama et al., "Extraction of lung region from 3D thoracic CT images with diffuse pulmonary diseases by use of graph cut and statistical atlas" IEICE, MI2012-88, 2013 (Partial Translation).

* cited by examiner

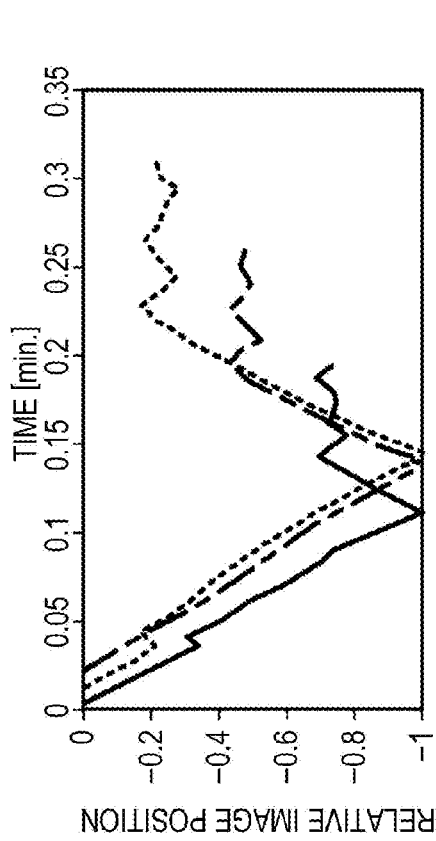
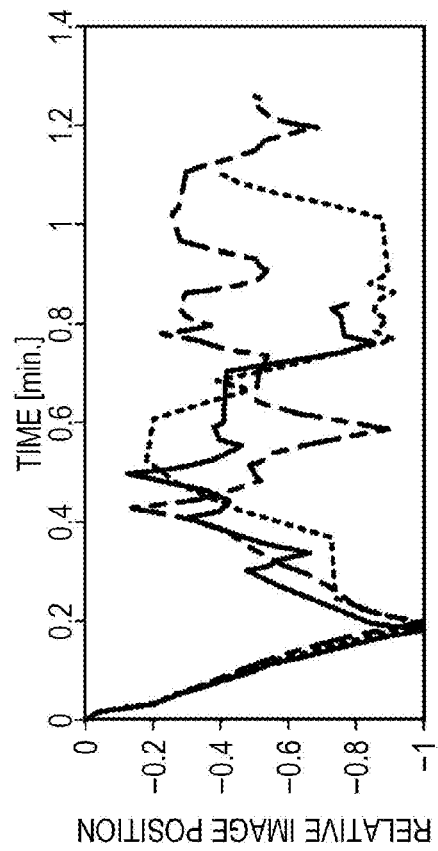
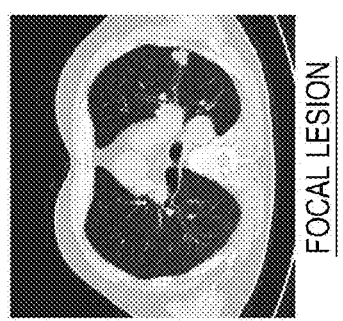
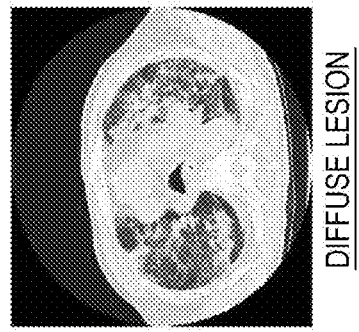
FIG. 2A
FIG. 2B

DIFFUSE LESION
NON-UNIFORM WEIGHTING FROM CENTER OF REGION OF INTEREST

FOCAL LESION
UNIFORM WEIGHTING WITHIN REGION OF INTEREST

LESION DETERMINATION APPARATUS, SIMILAR CASE SEARCHING APPARATUS, LESION DETERMINATION METHOD, SIMILAR CASE SEARCHING METHOD, AND NON-TRANSITORY COMPUTER-READABLE STORAGE MEDIUM

CROSS REFERENCE TO RELATED APPLICATION

This application is a continuation application of PCT/JP2014/003236, filed on Jun. 17, 2014, which claims priority to Japanese Patent Application No. 2013-160366, filed on Aug. 1, 2013, the contents of which are hereby incorporated by reference.

BACKGROUND OF THE INVENTION

1. Field of the Invention

The present disclosure relates to lesion determination techniques for determining whether an object part is a focal lesion or a diffuse lesion.

2. Description of the Related Art

Such a conventional apparatus is known that provides, as a similar case, the same mammographic image every time when the same region of interest is specified, even if the manner of specifying the region of interest varies depending on a doctor, who is a user (see PTL1 of Patent Literature).

CITATION LIST

Patent Literature

PTL 1: Unexamined Japanese Patent Publication No. 2010-130

Non-Patent Literatures

NPL 1: "Improvement of Tumor Detection Performance in Mammograms by Feature Selection from a Large Number of Features and Proposal of Fast Feature Selection Method" by M. Nemoto, A. Shimizu, Y. Hagihara, H. Kobata, S. Nawano, The IEICE (Institute of Electronics, Information and Communication Engineers of Japan) Transactions (Japanese Edition) D-II, Vol. J88-D-II, No. 2, pp. 416-426, February 2005

NPL 2: "Extraction of lung region from 3D thoracic CT images with diffuse pulmonary diseases by use of graph cut and statistical atlas" by R. Urayama, R. Xu, Y. Hirano, S. Kido, The Technical Report of The Proceeding of The Institute of Electronics, Information and communication Engineers of Japan, Medical Imaging (MI), Vol. 112, No. 411, pp. 135-138, January 2013

SUMMARY OF THE INVENTION

However, the configuration disclosed by the PTL1 is applicable to focal lesions only.

One non-limiting and exemplary embodiment provides a lesion determination apparatus for determining whether an object part is a focal lesion or a diffuse lesion. Additional benefits and advantages of the disclosed embodiments will be apparent from the specification and figures. The benefits and/or advantages may be individually provided by the various embodiments and features of the specification and drawings disclosure, and need not all be provided in order to obtain one or more of the same.

In one general aspect, the techniques disclosed here feature a lesion determination apparatus including: an image set acquiring unit configured to acquire a tomography image set containing a plurality of tomography images of an object part; an operation instruction receiving unit configured to receive a first operation instruction to view tomography images included in the plurality of tomography images in a first order in which a tomography image position number for identifying each of the tomography images increases, and a second operation instruction to view tomography images included in the plurality of tomography images in a second order in which the tomography image position number decreases; a number-of-images acquiring unit configured to acquire and record, on occurrence of a direction change that is either a first state in which the second operation instruction is received immediately after receipt of the first operation instruction or a second state in which the first operation instruction is received immediately after receipt of the second operation instruction, a number of one-directionally viewed images that is either a number of tomography images continuously viewed in response to continuous first operation instructions including the first operation instruction contained in the first state or a number of tomography images continuously viewed in response to continuous second operation instructions including the second operation instruction contained in the second state; and a locality determining unit configured to determine whether the object part is a focal lesion or a diffuse lesion based on a change in the number of one-directionally viewed images, wherein the tomography image position number is assigned such that a tomography image of a tomographic slice plane closer to a particular portion of the object part has a smaller tomography image position number.

Comprehensive or specific embodiments of these may be realized as a system, an apparatus, a method, an integrated circuit, a computer program, or computer-readable storage medium, or may be realized as any combination of a system, an apparatus, a method, an integrated circuit, a computer program and a storage medium. The computer-readable storage medium may include a non-volatile storage medium such as a CD-ROM (Compact Disc-Read Only Memory).

A lesion determination apparatus in accordance with the present disclosure can determine whether an object part is a focal lesion or a diffuse lesion.

BRIEF DESCRIPTION OF DRAWINGS

FIG. 2A is a diagram illustrating an image viewing history until a region of interest is set in a case of a focal lesion, FIG. 2B is a diagram illustrating an image viewing history until a region of interest is set in a case of a diffuse lesion;

DETAILED DESCRIPTION OF THE PREFERRED EMBODIMENTS

Figure 1:
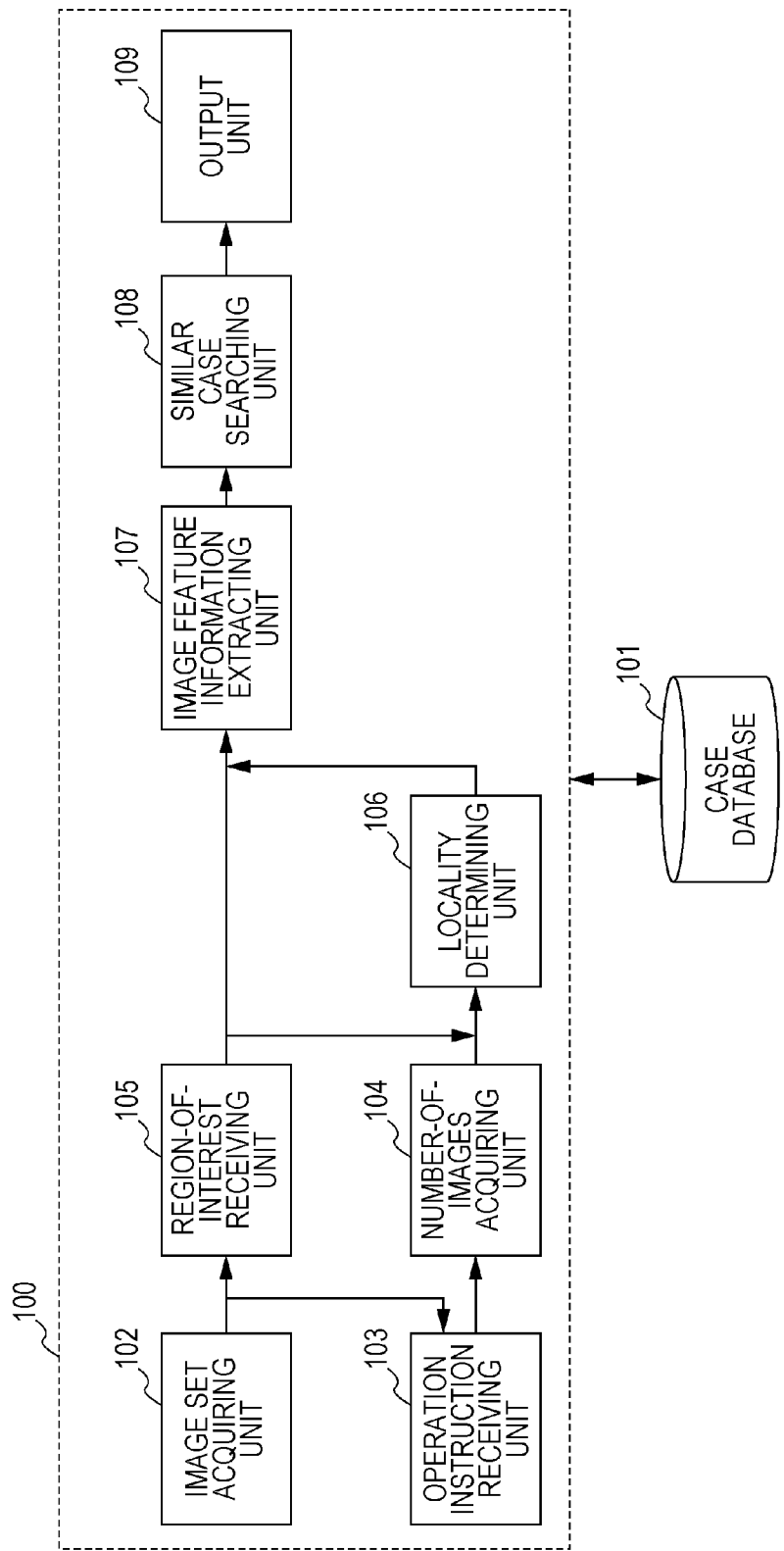
FIG. 1 is a block diagram illustrating a functional configuration of a similar case searching apparatus in accordance with a first exemplary embodiment.

Underlying Knowledge Forming Basis of the Present Disclosure

Recently, in the field of diagnostic imaging, digitalization of photographed images and image interpretation reports has been progressed, and it is easy for doctors to share a large amount of data items. As one of secondary uses of these data items, such an effort is expected that supports a decision-making concerning diagnosis by presenting a similar case with respect to an interpreting image, which is an object to be diagnosed, from stored data items.

In searching medical images, it is a general method to specify a region of interest in an image by a user, and to search an image having similar image feature information to that in the specified region of interest. In this method, however, since the region of interest contains an image region other than a lesion focused by the user, there is a problem that a search result may not always be an image similar to the lesion. As a convention technique to solve this problem, PTL 1 discloses a technique which performs a process of extracting a lesion region from a region of interest specified by a user, and then searches an image having image feature information similar to that of the extracted lesion region. That is, according to the method described in PTL 1, even if the setting of the region of interest varies depending on the user, it is possible to search a case similar to the lesion as far as the lesion region is contained in the region of interest.

Here, lesions are divided, when attention is focused on their distribution states, into focal lesions and diffuse lesions. The focal lesion is a lesion that is concentrated on a restricted area of an organ like a node or tumor mass. On the other hand, the diffuse lesion is a lesion that is spread widely in an organ like a wide range of ground glass opacity.

When a region of interest is set in a certain medical image to search a similar case, the region of interest can be set so as to cover an entire lesion in the case of a focal lesion. On the other hand, in the case of a diffuse lesion in which the lesion extends throughout the image, it is difficult to specify the entire lesion, and thus a region of interest is set in a part of the lesion. However, in the method as disclosed, for example, in PTL1, it is not distinguished whether the object lesion is a focal lesion or a diffuse lesion. Accordingly, when a region of interest is set in a part of a lesion which is spread widely in an organ, like a diffuse lesion, image feature information of the entire lesion cannot be properly extracted, so that accuracy of searching a similar case reduces.

Therefore, a first aspect of the present disclosure provides a lesion determination apparatus including: an image set acquiring unit configured to acquire a tomography image set containing a plurality of tomography images of an object part; an operation instruction receiving unit configured to receive a first operation instruction to view tomography images included in the plurality of tomography images in a first order in which a tomography image position number for identifying each of the tomography images increases, and a second operation instruction to view tomography images included in the plurality of tomography images in a second order in which the tomography image position number decreases; a number-of-images acquiring unit configured to acquire and record, on occurrence of a direction change that is either a first state in which the second operation instruction is received immediately after receipt of the first operation instruction or a second state in which the first operation instruction is received immediately after receipt of the second operation instruction, a number of one-directionally viewed images that is either a number of tomography images continuously viewed in response to continuous first operation instructions including the first operation instruction contained in the first state or a number of tomography images continuously viewed in response to continuous second operation instructions including the second operation instruction contained in the second state; and a locality determining unit configured to determine whether the object part is a focal lesion or a diffuse lesion based on a change in the number of one-directionally viewed images, wherein the tomography image position number is assigned such that a tomography image of a tomographic slice plane closer to a particular portion of the object part has a smaller tomography image position number.

With this aspect, it is possible to determine whether an object part is a focal lesion or a diffuse lesion from a viewing history of the tomography image set.

A second aspect of the present disclosure provides the lesion determination apparatus of the first aspect, wherein the locality determining unit determines that the object part is a focal lesion when the number of one-directionally viewed images has monotonically decreased with occurrence of the direction change, and otherwise determines that the object part is a diffuse lesion.

A third aspect of the present disclosure provides the lesion determination apparatus of the second aspect, wherein the locality determining unit excludes the number of one-directionally viewed images from consideration for determination when the number of one-directionally viewed images is equal to or smaller than a predetermined number.

A fourth aspect of the present disclosure provides the lesion determination apparatus of the first aspect, wherein the locality determining unit sets, as a predetermined threshold value, the number of one-directionally viewed images at a third direction change counted from a start of displaying the tomography image set, and determines that the object part is a focal lesion when the number of one-directionally viewed images at each of a fourth and subsequent direction changes is equal to or smaller than the predetermined threshold value, and otherwise determines that the object part is a diffuse lesion.

A fifth aspect of the present disclosure provides the lesion determination apparatus of the first aspect, wherein when a new direction change has occurred again within a predetermined period of time from a previous direction change, the number-of-images acquiring unit determines that the new direction change and the previous direction change did not occur.

A sixth aspect of the present disclosure provides a similar case searching apparatus for searching a similar case from a case database in which a plurality of case data items containing medical images have been registered, the similar case searching apparatus including: the lesion determination apparatus of the first aspect; a region-of-interest receiving unit configured to receive a setting of a region of interest with respect to the tomography images; an image feature information extracting unit configured to extract image feature information from the region of interest when the locality determining unit determines that the object part is a focal lesion, and configured to extract image feature information from an image region including both the region of interest and a region outside the region of interest when the locality determining unit determines that the object part is a diffuse lesion; and a similar case searching unit configured to search a similar case data item from the case database by comparing the image feature information extracted by the image feature information extracting unit to image feature information extracted from medical images contained in case data items registered in the case database.

With this aspect, in a case of a diffuse lesion, image feature information in a lesion region can be more appropriately extracted. Accordingly, it is possible to perform a highly accurate similar case search.

A seventh aspect of the present disclosure provides the similar case searching apparatus of the sixth aspect, wherein the image feature information extracting unit extracts image feature information from an entire region of an organ including the region of interest when the locality determining unit determines that the object part is a diffuse lesion.

With this aspect, even when a small number of cases are stored in the case database, it becomes possible to search a similar case consistent with a search intention with respect to a diffuse lesion.

An eighth aspect of the present disclosure provides the similar case searching apparatus of a sixth aspect, wherein the region-of-interest receiving unit receives the setting of the region of interest only when the locality determining unit determines that the object part is a focal lesion.

A ninth aspect of the present disclosure provides the similar case searching apparatus of the sixth aspect, further including an image weight setting unit configured to weight pixel values of the image in which the region of interest has been set in such a manner that the region of interest becomes a center of weighting when the locality determining unit determines that the object part is a diffuse lesion.

A tenth aspect of the present disclosure provides the similar case searching apparatus of any of the sixth to ninth aspects, further including an output unit configured to output the case data item obtained by the similar case searching unit to outside.

An eleventh aspect of the present disclosure provides a lesion determination method including the steps of: acquiring a tomography image set containing a plurality of tomography images of an object part; receiving a first operation instruction to view tomography images included in the plurality of tomography images in a first order in which a tomography image position number for identifying each of the tomography images increases, and a second operation instruction to view tomography images included in the plurality of tomography images in a second order in which the tomography image position number decreases; acquiring and recording, on occurrence of a direction change that is either a first state in which the second operation instruction is received immediately after receipt of the first operation instruction or a second state in which the first operation instruction is received immediately after receipt of the second operation instruction, a number of one-directionally viewed images that is either a number of tomography images continuously viewed in response to continuous first operation instructions including the first operation instruction contained in the first state or a number of tomography images continuously viewed in response to continuous second operation instructions including the second operation instruction contained in the second state; and determining whether the object part is a focal lesion or a diffuse lesion based on a change in the number of one-directionally viewed images, wherein the tomography image position number is assigned such that a tomography image of a tomographic slice plane closer to a particular portion of the object part has a smaller tomography image position number.

An twelfth aspect of the present disclosure provides a similar case searching method for searching a similar case by a computer from a case database in which a plurality of case data items containing medical images have been registered, the method including: performing the lesion determination method of the eleventh aspect; receiving a setting of a region of interest with respect to the tomography images; extracting image feature information from the region of interest when it is determined by the lesion determination method that the object part is a focal lesion, and extracting image feature information from an image region including both the region of interest and a region outside the region of interest when it is determined by the lesion determination method that the object part is a diffuse lesion; and searching a similar case data item from the case database by comparing the extracted image feature information to image feature information extracted from medical images contained in case data items registered in the case database.

A thirteenth aspect of the present disclosure provides a non-transitory computer-readable storage medium having stored a program for causing a computer to execute the lesion determination method of the eleventh aspect.

A fourteenth aspect of the present disclosure provides a non-transitory computer-readable storage medium having stored a program for causing a computer to execute the similar case searching method of the twelfth aspect.

A fifteenth aspect of the present disclosure provides a lesion determination apparatus including: an operation instruction receiving unit configured to receive an operation instruction to view a plurality of tomography images having a common normal direction sequentially in a predetermined direction, and an operation instruction to view the plurality of tomography images sequentially in an opposite direction to the predetermined direction; and a locality determining unit configured to determine, on occurrence of a direction change in which a viewing direction is changed according an operation instruction received by the operation instruction receiving unit, that an object part is a focal lesion when a number of one-directionally viewed images has monotonically decreased, and is a diffuse lesion when the number of one-directionally viewed images has not monotonically decreased, where the number of one-directionally viewed images is a number of images of the tomography images having been viewed continuously in an identical direction until the occurrence of the direction change.

A sixteenth aspect of the present disclosure provides a similar case searching apparatus for searching a similar case from a case database in which a plurality of case data items containing medical images have been registered, the apparatus including: the lesion determination apparatus of the fifteenth aspect; a region-of-interest receiving unit configured to receive a setting of a region of interest with respect to the tomography images; an image feature information extracting unit configured to extract image feature information from the region of interest when the locality determining unit determines that the object part is a focal lesion, and configured to extract image feature information from an image region including both the region of interest and a region outside the region of interest when the locality determining unit determines that the object part is a diffuse lesion; and a similar case searching unit configured to search a similar case data item from the case database by comparing the image feature information extracted by the image feature information extracting unit to image feature information extracted from medical images contained in case data items registered in the case database.

A seventeenth aspect of the present disclosure provides the similar case searching apparatus of the sixteenth aspect, wherein the region-of-interest receiving unit receives the setting of the region of interest only when the locality determining unit determines that the object part is a focal lesion.

Terms used in the following exemplary embodiments will be described.

The "image feature information" includes feature information regarding a shape of an organ or a lesion part in a medical image, and feature information regarding brightness distribution in a medical image. For example, NPL 1 of the Non-Patent Literature discloses 490 kinds of features (feature information) as the image feature information. In the present disclosure also, the image feature information to be used includes several tens to several hundred kinds of image feature information which are predetermined for each medical image photographing apparatus (modality) used to photograph a medical image and for each target organ.

Further, the medical images in the present disclosure include ultrasound images, CT (Computed Tomography) images or MRI (Magnetic Resonance Imaging) images.

Further, the "focal lesion" is a lesion that is concentrated on a narrow area in an organ, and the "diffuse lesion" is a lesion that is spread over a wide area in an organ.

First Exemplary Embodiment

Configuration of Apparatus

FIG. 1 is a block diagram illustrating a functional configuration of similar case searching apparatus 100 in accordance with a first exemplary embodiment.

Similar case searching apparatus 100 in FIG. 1 is an apparatus which searches a similar case data item according to an image interpretation result by an image interpreter from case database 101 in which case data items containing medical images have been registered. As shown in FIG. 1, similar case searching apparatus 100 includes image set acquiring unit 102, operation instruction receiving unit 103, number-of-images acquiring unit 104, region-of-interest receiving unit 105, locality determining unit 106, image feature information extracting unit 107, similar case searching unit 108, and output unit 109. A lesion determination apparatus in accordance with the present disclosure includes image set acquiring unit 102, operation instruction receiving unit 103, number-of-images acquiring unit 104, and locality determining unit 106.

Hereinafter, details of each component of case database 101 and similar case searching apparatus 100 which are illustrated in FIG. 1 will be described in due order.

Case database 101 is a storage device including a hard disk, a memory, or the like, and has stored therein case data items including interpretation image data items providing an image interpreter with images to be interpreted, and image interpretation information corresponding to the interpretation image data items. Here, the interpretation image data items are image data items used for image diagnosis and stored in an electronic medium. Further, the image interpretation information is information associated with the interpretation image data items, and includes documentation data items such as interpretation results of the interpreted image data items, results of various examinations including biopsy undergone after image diagnosis, and results of clinical diagnosis.

Image set acquiring unit 102 acquires a tomography image set which is used by the image interpreter when making a diagnosis. The tomography image set is a plurality of tomography image groups obtained by slicing an object part of a human body toward a predetermined direction by, for example, CT or MRI. That is, the tomography image set includes a plurality of tomography images of an object part which are placed sequentially toward the predetermined direction. Image set acquiring unit 102 outputs the acquired tomography image set to operation instruction receiving unit 103 and region-of-interest receiving unit 105.

Operation instruction receiving unit 103 receives an operation instruction regarding a display order when the tomography image set is displayed on a display screen. Specifically, operation instruction receiving unit 103 receives an operation instruction to view the tomography images sequentially in the predetermined direction and an operation instruction to view the tomography images sequentially in an opposite direction to the predetermined direction. Then, operation instruction receiving unit 103 outputs a set of a viewing direction based on the operation instruction and a time at which the operation instruction has been received to number-of-images acquiring unit 104.

The operation instruction here may be performed by, for example, an output signal of an operation device such as a mouse. For example, in a case where a scroll wheel of a mouse is scrolled to operate display of tomography images, an operation instruction signal for scrolling the tomography images up may be used for, for example, display of tomography images in a sequential order from foot toward head, and in contrast to this, an operation instruction signal for scrolling the tomography images down may be used for, for example, display of tomography images in a sequential order from head toward foot. At this time, operation instruction receiving unit 103 acquires a scrolling direction of the mouse and a time at which its operation instruction has been received, and outputs the acquired information to number-of-images acquiring unit 104.

Number-of-images acquiring unit 104 counts the number of displayed tomography images. Then, number-of-images acquiring unit 104 receives information of the operation instruction from operation instruction receiving unit 103, and, when a direction change has occurred to change the viewing direction in response to the operation instruction, acquires and records a direction-change time indicating the occurring time of the direction change and a number of one-directionally viewed images which is the number of tomography images continuously viewed in one direction until the direction change occurred this time.

Region-of-interest receiving unit 105 acquires coordinates of a region of interest set with respect to a displayed tomography image, and outputs the acquired coordinates to locality determining unit 106. Here, the region of interest is a particular image region which is set in a displayed image when a case having an image morphology similar to that of this region is to be searched. Further, the region of interest is a region containing a plurality of pixels. The region of interest is specified, for example, as a rectangle or a circle. In the case of a rectangle, coordinates of a starting point and an ending point are output as coordinates of the region of interest.

Locality determining unit 106 refers, when it has acquired the coordinates of the region of interest from region-of-interest receiving unit 105, to the direction-change time and the number of one-directionally viewed images recorded by number-of-images acquiring unit 104, and determines whether the object part is a focal lesion or a diffuse lesion based on a change of the number of one-directionally viewed images associated with occurrence of the direction change. For example, locality determining unit 106 determines the object part as a focal lesion if the number of one-directionally viewed images has decreased monotonically along with occurrence of direction changes, and otherwise determines as a diffuse lesion. Locality determining unit 106 outputs the determination result to image feature information extracting unit 107.

Incidentally, each of the tomography images to be displayed may be identified by a tomography image position number. Moreover, the tomography image position number may be assigned such that a tomography image of a tomographic slice plane closer to a particular portion of the object part (i.e., the distance between a point indicating the particular portion and the tomographic slice plane is shorter) has a smaller tomography image position number.

Operation instruction receiving unit 103 may receive a first operation instruction to view tomography images included in the plurality of tomography images, which are to be displayed, in a first order in which the tomography image position number for identifying each tomography image increases, and a second operation instruction to view tomography images included in the plurality of tomography images, which are to be displayed, in a second order in which the tomography image position number decreases. Number-of-images acquiring unit 104 may acquire and record, on occurrence of a direction change that is either a first state in which the second operation instruction is received immediately after receipt of the first operation instruction or a second state in which the first operation instruction is received immediately after receipt of the second operation instruction, a number of one-directionally viewed images that is either a number of tomography images continuously viewed in response to continuous first operation instructions including the first operation instruction contained in the first state or a number of tomography images continuously viewed in response to continuous second operation instructions including the second operation instruction contained in the second state.

Here, reasons will be described as to why distinction between a focal lesion and a diffuse lesion is possible based on a change of the number of one-directionally viewed images.

FIGS. 2A and 2B illustrate diagrams each showing a history of viewing images plotted until a region of interest is set with respect to cases for a lung CT images. FIG. 2A shows the history in a case of a focal lesion, and FIG. 2B shows the history in a case of a diffuse lesion. Data items of three cases are plotted with respect to each of the focal lesion and the diffuse lesion. The vertical axis of each graph indicates relative image position, and the horizontal axis indicates operation time. Since each case differs in the number of tomography images from another, the vertical axis indicates relative image position. For example, the relative image position of value "0" means a first tomography image at the head side, and that of value −1 means a final image at the foot side.

It is found from comparison of the viewing histories that the cases of the focal lesion converge in amplitude (equivalent to the number of one-directional views) over time. This is because the region of interest is set within a small number of images, since the lesion region is concentrated on a local area. On the other hand, the cases of the diffuse lesion do not converge in amplitude over time. This is because the region of interest is set in a large number of images, since the diffuse region is distributed over a wide area.

Considering the above, it is possible to distinguish between a focal lesion and a diffuse lesion by observing whether or not the image viewing history until setting a region of interest converges. The convergence can be determined, for example, by checking whether or not the amplitude, or the number of one-directionally viewed images, decreases monotonically in, for example, the image viewing history.

Figure 3:
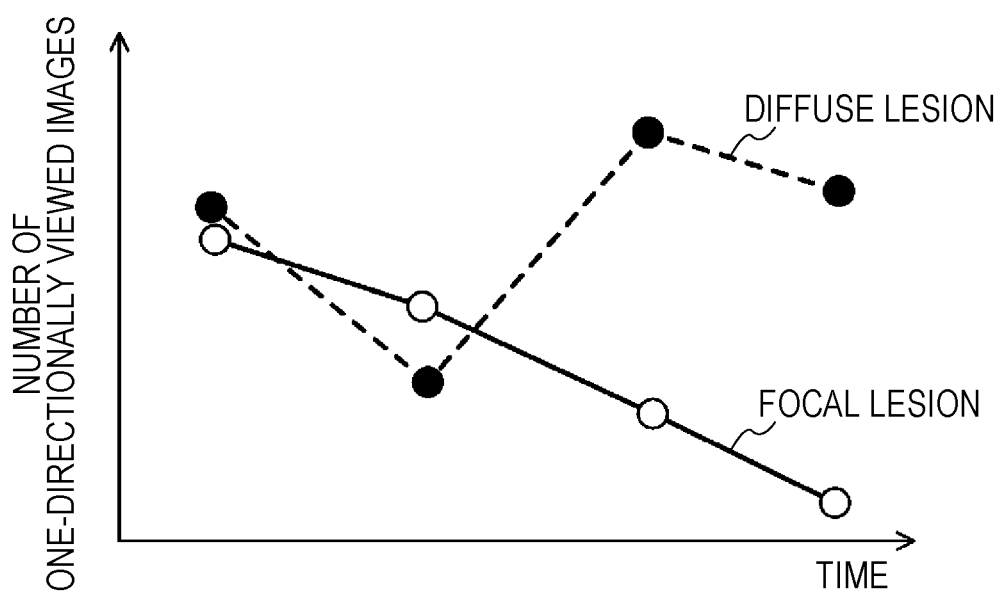
FIG. 3 is a conceptual diagram showing a chronological change in the number of one-directionally viewed images.

FIG. 3 is a conceptual diagram expressing some viewing histories shown in FIGS. 2A and 2B as chronological changes in the number of one-directionally viewed images. As shown in FIG. 3, the number of one-directionally viewed images decreases monotonically in the case of the focal lesion, but does not decrease monotonically in the case of the diffuse lesion. In this way, by utilizing the chronological change in the number of one-directionally viewed images, it is possible to distinguish between a focal lesion and a diffuse lesion. A specific method of determining a focal lesion or a diffuse lesion will be described in detail later.

Incidentally, although, in the present exemplary embodiment, the direction-change time and the number of one-directionally viewed images are recorded as a viewing history of the tomography image set, a change of the number of one-directionally viewed images associated with occurrence of a direction change may be recognized in order to perform locality determination. Accordingly, it may not always be necessary to record the direction-change time itself. For example, number-of-times information indicating how many times the direction change occurred, and the number of one-directionally viewed images may be recorded as the viewing history.

Referring back to FIG. 1, image feature information extracting unit 107 extracts image feature information from an image region within the region of interest obtained from the region-of-interest receiving unit 105 when the locality determining unit 106 determines that the object part is a focal lesion, and, on the other hand, extracts image feature information from a region outside the region of interest in addition to an image region within the region of interest when the locality determining unit 106 determines that the object part is a diffuse lesion. Image feature information extracting unit 107 outputs the extracted image feature information to similar case searching unit 108. A method of extracting the image feature information will be described later.

In a case of a focal lesion, which is concentrated on a narrow area in an organ, the region of interest is set to surround the entire lesion. Accordingly, when a similar case with respect to a focal lesion is to be searched, it is necessary to search a case which is similar in an image area within the region of interest. On the other hand, in a case of a diffuse lesion, which spreads over a wide area in an organ, the region of interest is set with respect to a part of the lesion. Accordingly, when a similar case with respect to a diffuse lesion is to be searched, it is necessary to search a similar case by extracting image feature information not only from the region of interest, but also from a region outside the region of interest.

Similar case searching unit 108 searches a similar case data item from case database 101 by comparing the image feature information obtained by image feature information extracting unit 107 and image feature information extracted from medical images contained in the case data items registered in case database 101. A specific method of obtaining a similar case will be described later.

Output unit 109 outputs the case data item obtained by the similar case searching unit 108 to the outside of similar case searching apparatus 100, for example, an output medium.

Next, operations of similar case searching apparatus 100 configured as above will be described.

Operations

Figure 4:
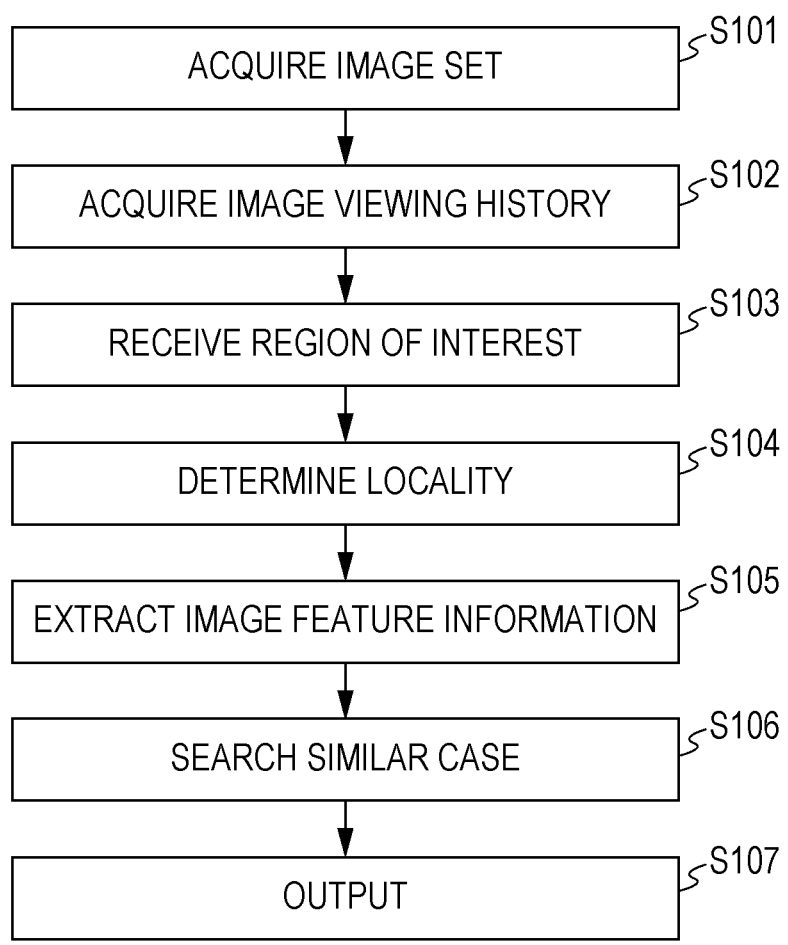
FIG. 4 is a flowchart illustrating a flow of processes performed by the similar case searching apparatus in accordance with the first exemplary embodiment.

FIG. 4 is a flowchart illustrating an overall flow of processes performed by similar case searching apparatus 100 shown in FIG. 1.

First, image set acquiring unit 102 acquires a tomography image set which is used by an image interpreter when making a diagnosis (step S101). This tomography image set may be acquired from case database 101 or may be acquired from another medium. Image set acquiring unit 102 notifies operation instruction receiving unit 103 and region-of-interest receiving unit 105 of the acquired tomography image set.

Next, each of operation instruction receiving unit 103 and number-of-images acquiring unit 104 acquires the viewing history of the displayed tomography image set, that is, the direction-change time and the number of one-directionally viewed images (step S102).

Figure 5:
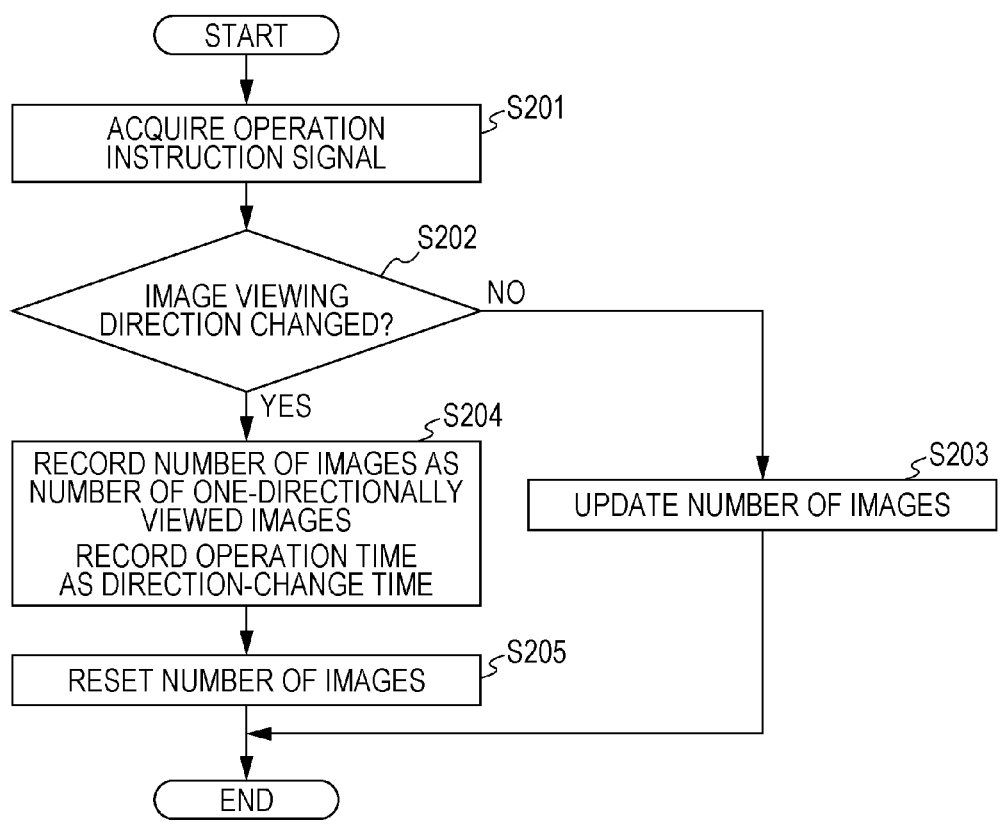
FIG. 5 is a flowchart illustrating a process performed each time when a new tomography image is displayed in step S102 shown in FIG. 4.
Figure 6B:
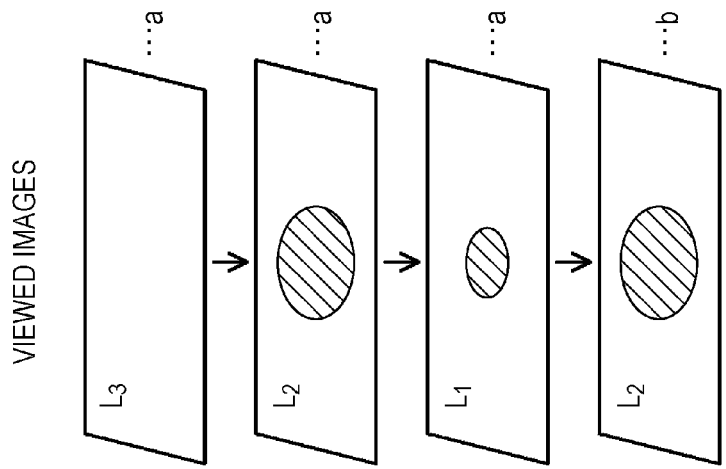
FIGS. 6A and 6B are diagrams for explaining an example of an operation instruction signal.
Figure 6A:
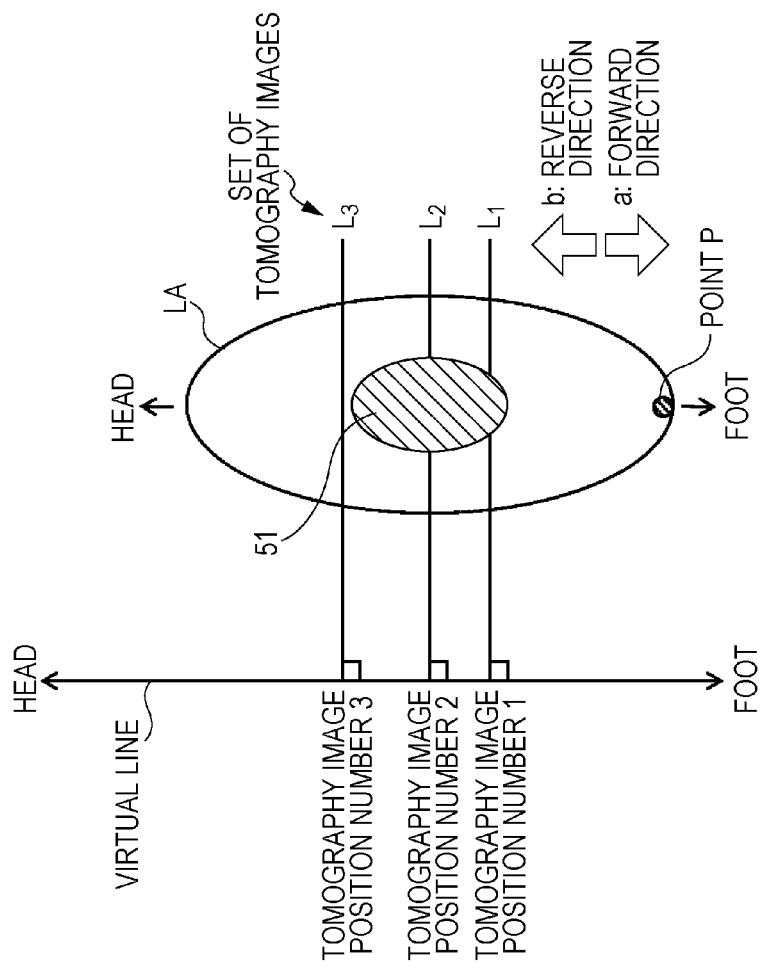

FIG. 5 is a flowchart illustrating a process performed each time when a new tomography image is displayed in step S102. First, operation instruction receiving unit 103 obtains an operation instruction signal (step S201). FIGS. 6A and 6B are diagrams for explaining an example of an operation instruction signal. As shown in FIG. 6A, a tomography image set containing tomography images L1 to L3 is given with respect to lesion 51 in lung area LA.

Further, each tomography image may be corresponded to a tomography image position number assigned sequentially along a virtual line to identify the tomography image. The virtual line may, for example, be a straight line perpendicular to the tomographic slice planes of the tomography images of the object part (e.g., lung).

A smallest tomography image position number (e.g., "1") may be assigned to a particular tomography image of the object part, for example, a tomography image of a tomographic slice plane nearest to foot, and the tomography image position number of the tomography image may be increased as the tomographic slice plane becomes farther from the particular tomography image. In contrast, a smallest tomography image position number (e.g., "1") may be assigned to a particular tomography image of the object part, for example, a tomography image of a tomographic slice plane nearest to head, and the tomography image position number of the tomography image may be increased as the tomographic slice plane becomes farther from the particular tomography image.

FIG. 6A shows an example in which the smallest tomography image position number "1" is assigned to tomography image L1 which is nearest to point P in lung area LA (a point nearest to foot in lung area LA) among tomography images L1, L2 and L3. Further, the second smallest tomography image position number "2" is assigned to tomography image L2 which is the second nearest to point P in lung area LA among tomography images L1, L2 and L3. Furthermore, the third smallest tomography image position number "3" is assigned to tomography image L3 which is the third nearest to point P in lung area LA among tomography images L1, L2 and L3. It may be needless to say that a point nearest to head in lung area LA may be represented as point P.

A shown in FIG. 6B, when a user viewed the tomography image set in the order of tomography image L3→tomography image L2→tomography image L1→tomography image L2, that is, in the order of tomography image position number 3→tomography image position number 2→tomography image position number 1→tomography image position number 2, signals a→a→a→b are obtained as operation instruction signals. Here, "a" denotes a forward direction, and "b" denotes a reverse direction. A signal used as the operation instruction signal may, for example, be an operation signal of a mouse.

Next, number-of-images acquiring unit 104 determines whether or not the viewing direction has been changed by using the operation instruction signal received by operation instruction receiving unit 103 in step S201 from the viewing direction instructed by using a previously received operation instruction signal (step S202). If the viewing direction has not been changed (NO in step S202), the process proceeds to step S203 to update the recorded number of images, or to increment the number of images by 1. When an operation instruction signal is received for the first time, it may be determined that there is no change of the operation instruction signal, and the process may proceed to step S203. On the other hand, if the viewing direction has been changed (YES in step S202), the process proceeds to step S204 to record the recorded number of images as the number of one-directionally viewed images, and to record the operation time at this time as a direction-change time. In the case of FIGS. 6A and 6B, the number of one-directionally viewed images is 3. Then, the number of images is reset in step S205. Specifically, the number of images is set to 1.

Figures 7A, 7B:
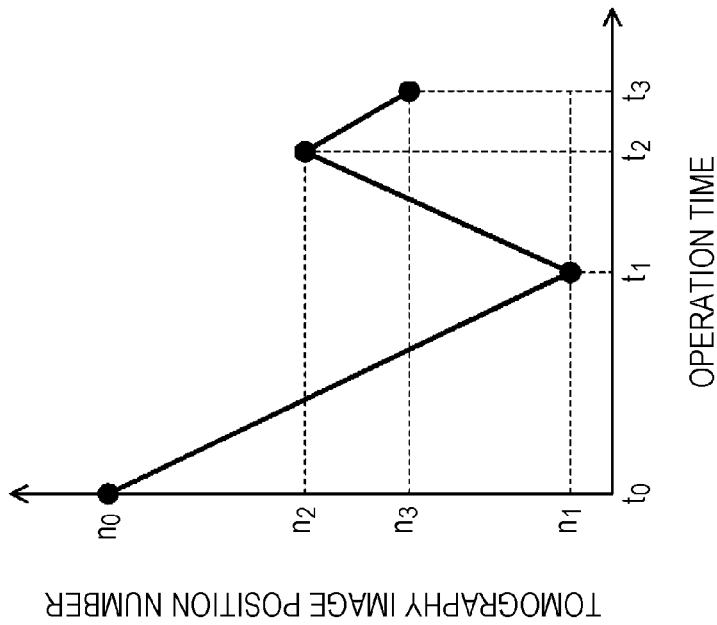
FIGS. 7A and 7B are diagrams for explaining a result of the process in the flow in FIG. 5.

FIGS. 7A and 7B are conceptual diagrams showing a result of the process shown in FIG. 5. When there is a viewing history as shown in FIG. 7A (starting time t0, region-of-interest setting time t3, direction-change times t1, t2 and t3), viewing history data items as shown in FIG. 7B are recorded by repetitively performing the process shown in FIG. 5. For example, a number of one-directionally viewed images |n2−n1| is recorded at direction-change time t2.

Incidentally, to eliminate an erroneous operation of a mouse or the like, if a direction change has occurred again within a very short time from a previous direction change, these direction changes may be eliminated from the viewing history. That is, when images are viewed by operating a mouse or the like, such a case may sometimes occur that the viewing direction is changed regardless of the user's intention due to, for example, an erroneous scrolling operation. In this case, if the number of one-directionally viewed images is recorded in step S204 in FIG. 5, there is a possibility that the locality would be erroneously determined.

Further, if such erroneous operation has occurred, it is highly probable that the user would correct the operation and thus the viewing direction would change again within a very short time. Accordingly, when a new direction change has occurred within a predetermined period of time from a previous direction change, number-of-images acquiring unit 104 may determine that the previous direction change and the new direction change did not actually occur, and may continue updating the number of images. This makes it possible to prevent an erroneous locality determination from being caused due to a user's erroneous operation. The predetermined period of time set here may be an average time required from an erroneous operation of a mouse to a correction for the operation, for example, about 0.1 second.

Referring back to the flow in FIG. 4, region-of-interest receiving unit 105 acquires coordinates of a region of interest set with respect to a displayed tomography image, and notifies locality determining unit 106 of the acquired coordinates of the region of interest (step S103).

Figure 8:
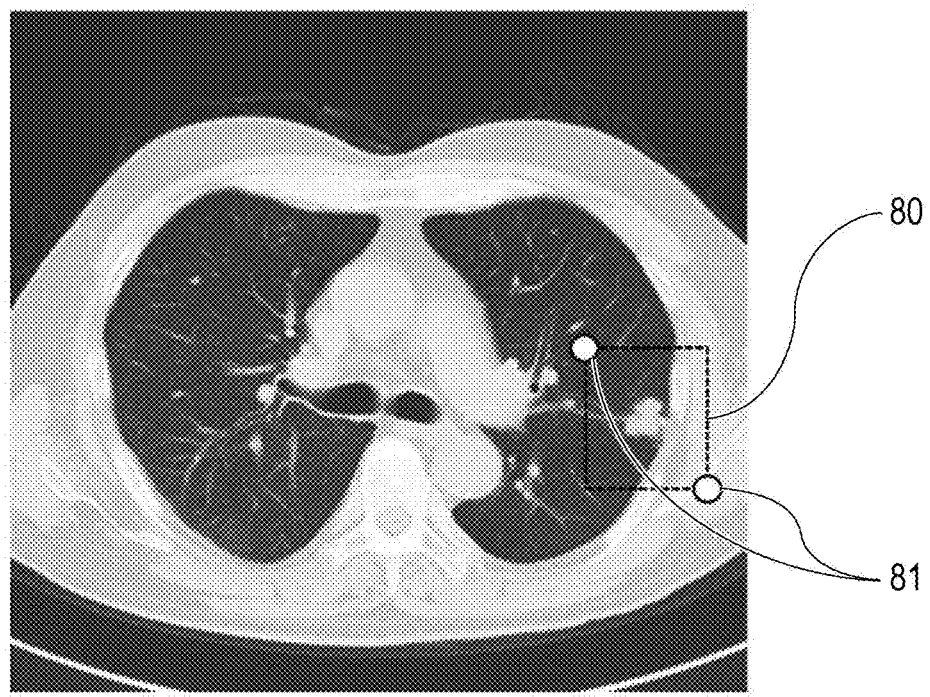
FIG. 8 illustrates an example of setting a region of interest.

An example manner of setting a region of interest is shown in FIG. 8. The region of interest is an arbitrary region set in a tomography image by a user. Similar case searching apparatus 100 searches a case which has an image feature similar to an image feature in the set region of interest. FIG. 8 shows an example of setting a region of interest as a rectangle. In this example, region-of-interest receiving unit 105 may acquire peak coordinates 81 of region of interest 80, and notify locality determining unit 106 of acquired peak coordinates 81 of region of interest 80. Further, as another manner, a region of interest may be set as a circle. In this case, region-of-interest receiving unit 105 may acquire center coordinates and radius of the circle, and notify locality determining unit 106 acquired center coordinates and radius of the circle.

Next, locality determining unit 106 refers to the image viewing history, that is, the direction-change time and the number of one-directionally viewed image, recorded in step S102, and determines whether the object part is a focal lesion or a diffuse lesion (step S104).

Figure 9:
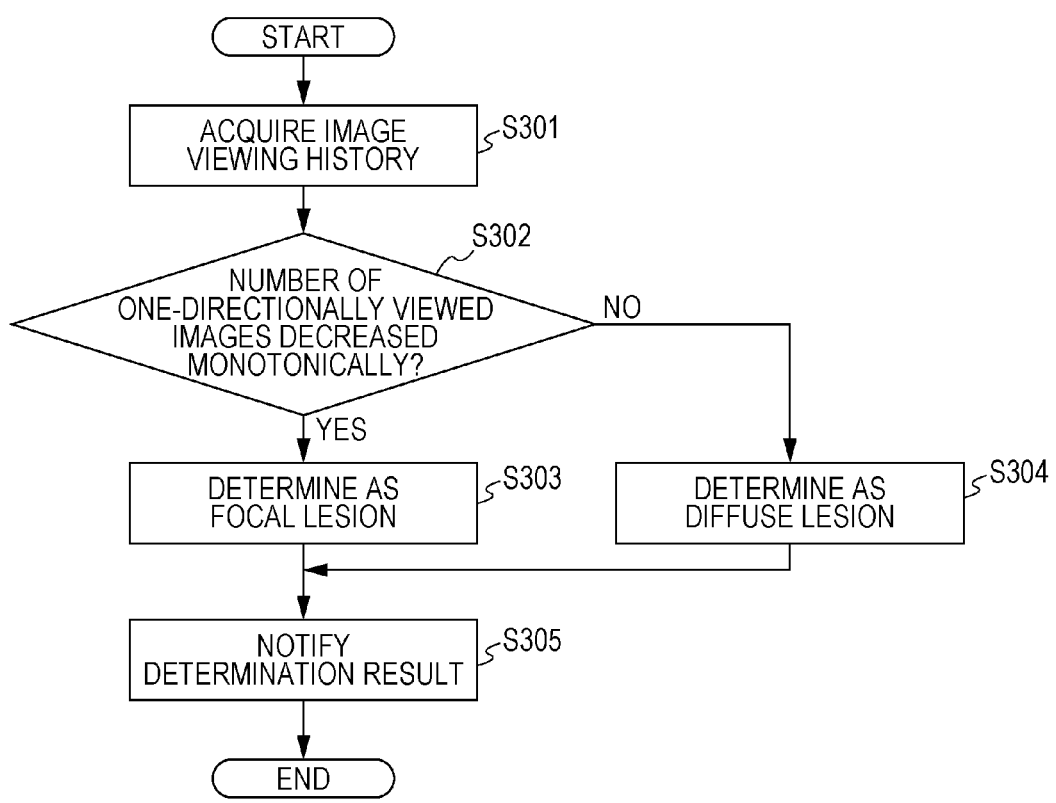
FIG. 9 is a flowchart illustrating an example of locality determination process.

FIG. 9 is a flowchart illustrating an example of step S104, that is, a locality determination process performed in locality determining unit 106.

First, locality determining unit 106 acquires the image viewing history, that is, the direction-change time and the number of one-directionally viewed images (step S301). Then, locality determining unit 106 determines whether or not the number of one-directionally viewed images has decreased monotonically with the advance of the direction-change time (step S302). Locality determining unit 106 determines that the object part is a focal lesion (step S303) when the number of one-directionally viewed images has decreased monotonically (YES in step S302), and that the object part is a diffuse lesion (step S304) when the number of one-directionally viewed images has not decreased monotonically (NO in step S302). Determination of a monotonic decrease may, for example, be performed as follows. That is, the number of one-directionally viewed image at each direction-change time may be subtracted from the number of one-directionally viewed image at a previous direction-change time, and it may be determined that the number of one-directionally viewed images has monotonically decreased if all difference values of the subtraction result are positive values, and as has not monotonically decreased otherwise.

Incidentally, a number of one-directionally viewed images which is equal to or smaller than a predetermined number may be excluded from an object to be determined. For example, there is a case that a user performs such a search action as to view several images repeatedly many times just before setting a region of interest. In such a case, the number of one-directionally viewed images is expected to slightly increase or decrease. However, since this is not an action caused by a focal lesion or a diffuse lesion, locality determination using information including this data item may cause a wrong determination result with high probability. Accordingly, a more accurate locality determination can be performed by excluding the data item regarding the number of one-directionally viewed images equal to or smaller than the predetermined number from the objects of the locality determination. The predetermined number to be set here may be a number of images that a user usually views repeatedly in setting a region of interest, and may, for example, be 5.

Then, locality determining unit 106 notifies image feature information extracting unit 107 of the determination result in step S303 or step S304 (step S305).

Figure 10:
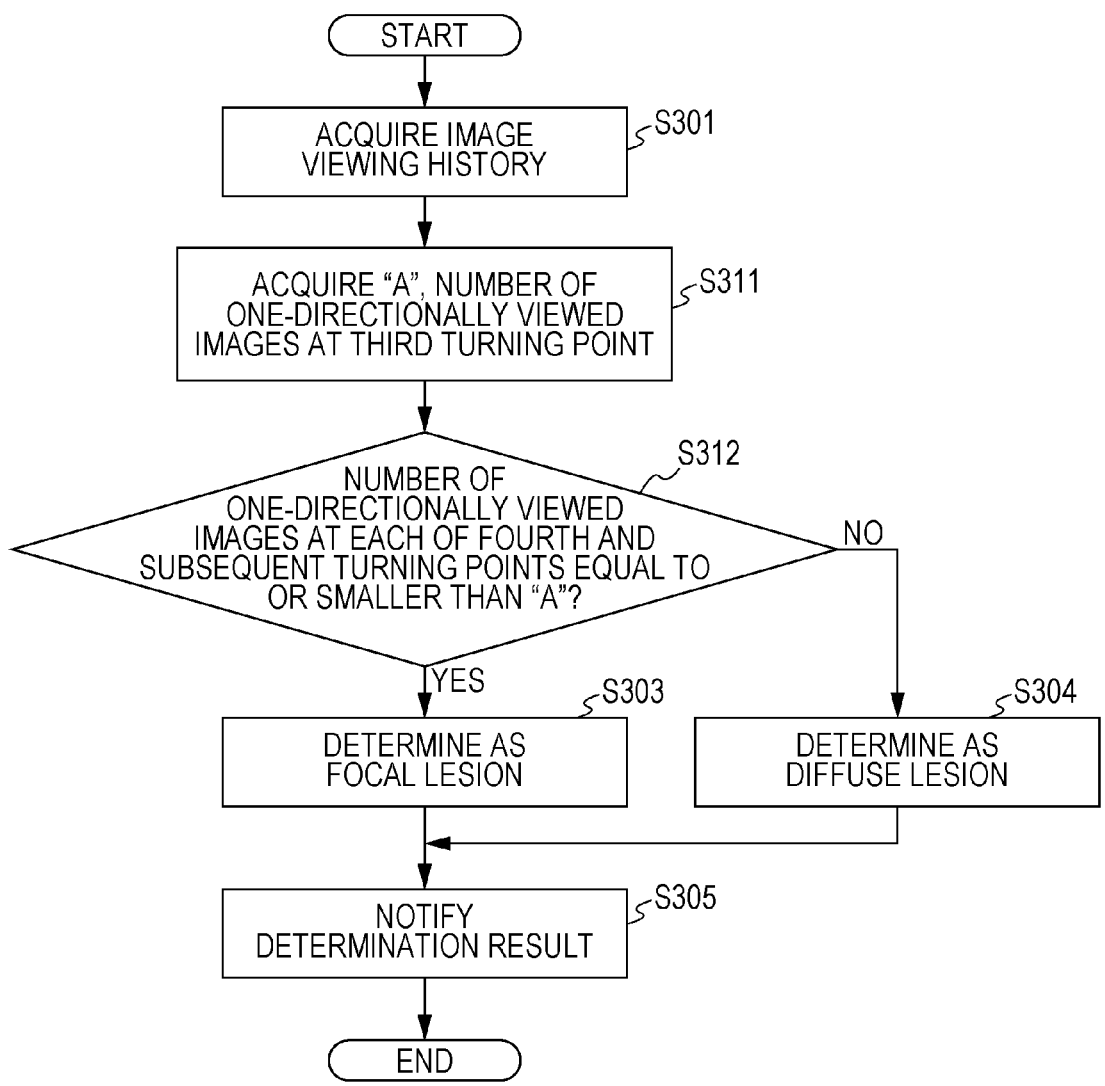
FIG. 10 is a flowchart illustrating another example of locality determination process.
Figure 11A:
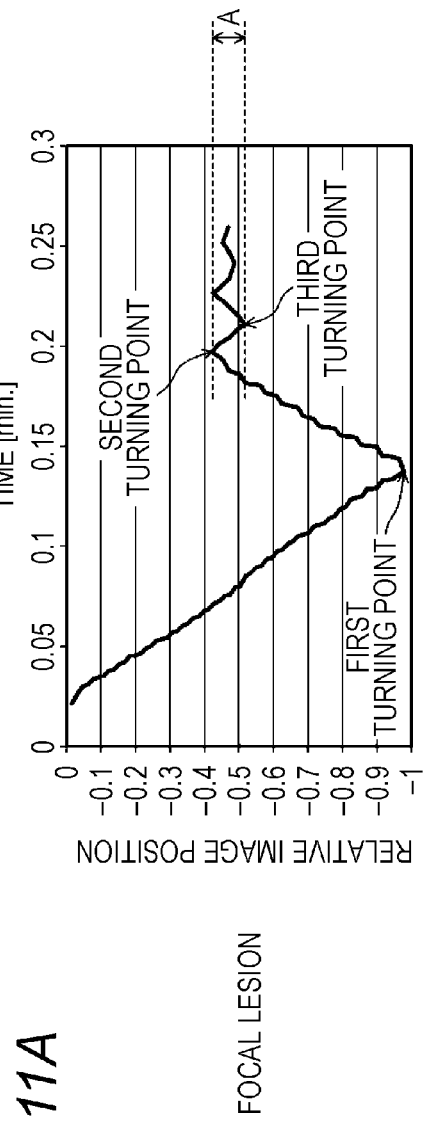
FIG. 11A is a diagram illustrating an image viewing history until a region of interest is set in a case of a focal lesion.
Figure 11B:
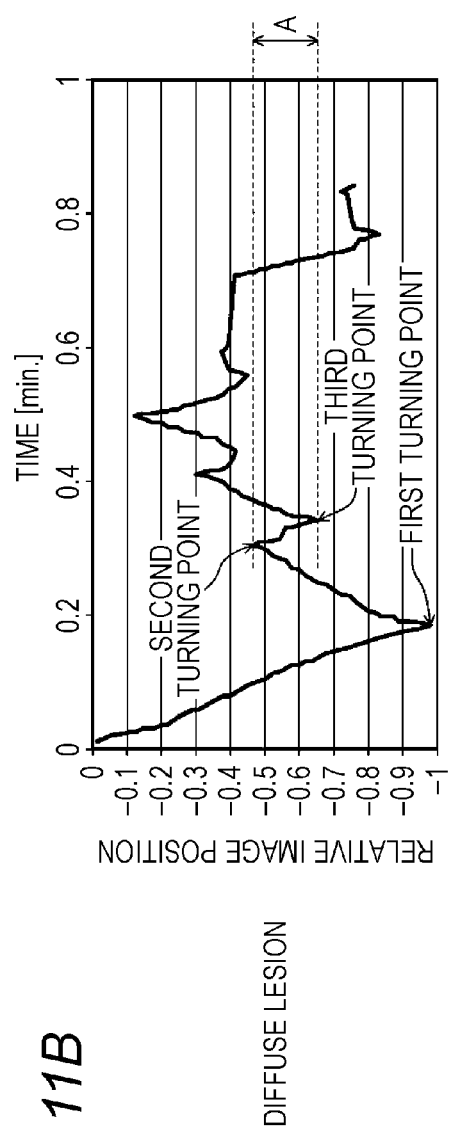
FIG. 11B is a diagram illustrating an image viewing history until a region of interest is set in a case of a diffuse lesion.

Note that, it is possible to determine a focal lesion by using the image viewing history by a different method than the locality determination method. FIG. 10 is a flowchart illustrating another example of step S104, that is, locality determination process performed in locality determining unit 106. In FIG. 10, the same steps as those in FIG. 9 are indicated by the same reference marks. Further, FIGS. 11A and 11B illustrate diagrams for explaining the method shown in FIG. 10, or, more specifically, graphs each showing an example of image viewing history similarly to FIGS. 2A and 2B. FIG. 11A shows a graph in a case of a focal lesion, and FIG. 11B shows a graph in a case of a diffuse lesion.

To interpret tomography images, a user first views all images starting from a first image to a last image, and then returns to an image containing a lesion to view the lesion in detail. That is, referring to FIGS. 11A and 11B, it is thought that a first turning point indicates a time point at which all images have been reviewed, a second turning point indicates an upper limit of the position of the lesion, and a third turning point indicates a lower limit of the position of the lesion.

Here, as shown in FIG. 11A, since the lesion concentrates on one location in the case of a focal lesion, tomography images viewed after the third turning point are limited to those between an image position at the second turning point (the upper limit location of the lesion) and an image position at the third turning point (the lower limit position of the lesion). In other words, after the third turning point, the number of one-directionally viewed images will not exceed the number of one-directionally viewed images at the third turning point. On the other hand, as shown in FIG. 11B, since the lesion spreads widely in an organ in the case of a diffuse lesion, it can be said that tomography images viewed after the third turning point will not necessarily be limited to those between an image position at the second turning point (the upper limit position of the lesion) and an image position at the third turning point (the lower limit position of the lesion). The method shown in FIG. 10 utilizes this characteristic difference between a focal lesion and a diffuse lesion.

First, locality determining unit 106 acquires the image viewing history, that is, the direction-change time and the number of one-directionally viewed images (step S301). Then, locality determining unit 106 acquires the number of one-directionally viewed images at the third turning point as threshold value "A" from the image viewing history acquired in step S301 (step S311). This threshold value "A" is the number of one-directionally viewed images at a third direction change counted from the start of displaying the tomography image set, and corresponds to the number of tomography images viewed after the second turning point until the third turning point.

Next, locality determining unit 106 determines whether or not the number of one-directionally viewed images at each of the fourth and the subsequent turning points is equal to or smaller than threshold value "A" (step S312). Then, locality determining unit 106 determines the lesion as a focal lesion when the number of one-directionally viewed images is equal to or smaller than "A" at all of the fourth and the subsequent turning points (step S303), and determines as a diffuse lesion when the number of one-directionally viewed images exceeds "A" at one or more of the fourth and the subsequent turning points (step S304).

Then, locality determining unit 106 notifies image feature information extracting unit 107 of the determination result in step S303 or step S304 (step S305).

Referring back to the flow in FIG. 4, image feature information extracting unit 107 extracts image feature information from an image region within the region of interest acquired by region-of-interest receiving unit 105 when the determination result by locality determining unit 106 is a focal lesion, and extracts image feature information from a region outside the region of interest in addition to the image region within the region of interest when the determination result by locality determining unit 106 is a diffuse lesion (step S105).

Here, the region outside the region of interest may, for example, be an entire organ to be diagnosed (an entire lung area in a case of lung) in the image in which the region of interest has been set. For example, the lung area can be automatically extracted by using the image processing method disclosed by NPL 2 of the Non-Patent Literature. Since a diffuse lesion occupies a wide area in an organ, it is possible, by extracting image feature information from the entire organ, to more accurately search a similar case matched to a lesion region in an image in which a region of interest has been set.

Then, similar case searching unit 108 acquires a similar case data item from case database 101 by using the image feature information obtained by image feature information extracting unit 107 (step S106). For example, a specific method of calculating similarity may be to calculate, as similarity, a cosine distance between an image feature information vector which is a vector representation of the image feature information obtained by image feature information extracting unit 107 and an image feature information vector in a region of interest of a medical image contained in another case data item stored in case database 101, and may be to extract a case giving a cosine distance equal to or larger than a threshold value as a similar case.

Output unit 109 outputs the case data item obtained by similar case searching unit 108 to the outside of similar case searching apparatus 100 (step S108).

By performing the process as shown in FIG. 4, as described hereinabove, similar case searching apparatus 100 can determine whether or not a search object part is a focal lesion or a diffuse lesion, and properly extract, by using this determination result, image feature information of the lesion region. Accordingly, it is possible to perform a highly accurate similar case search.

Incidentally, region-of-interest receiving unit 105 may receive a setting of a region of interest only when locality determining unit 106 has determined the object part as a focal lesion. That is, according to the present exemplary embodiment, for example, image feature information is extracted not only from the region of interest, but also from the entire area of an organ in the case of a diffuse lesion. In this case, it is not necessary to set a region of interest with respect to a diffuse lesion. Accordingly, for example, such a control may be performed that enables, when a similar case search button is pressed down, a region of interest to be set only when the object part has been determined as a focal lesion. With this control, it is possible to reduce the steps of the operation procedure with respect to a diffuse lesion.

As described hereinabove, according to the present exemplary embodiment, a highly accurate similar case search is possible even for cases in which focal lesions and diffuse lesions are mixed.

Second Exemplary Embodiment

Figure 12:
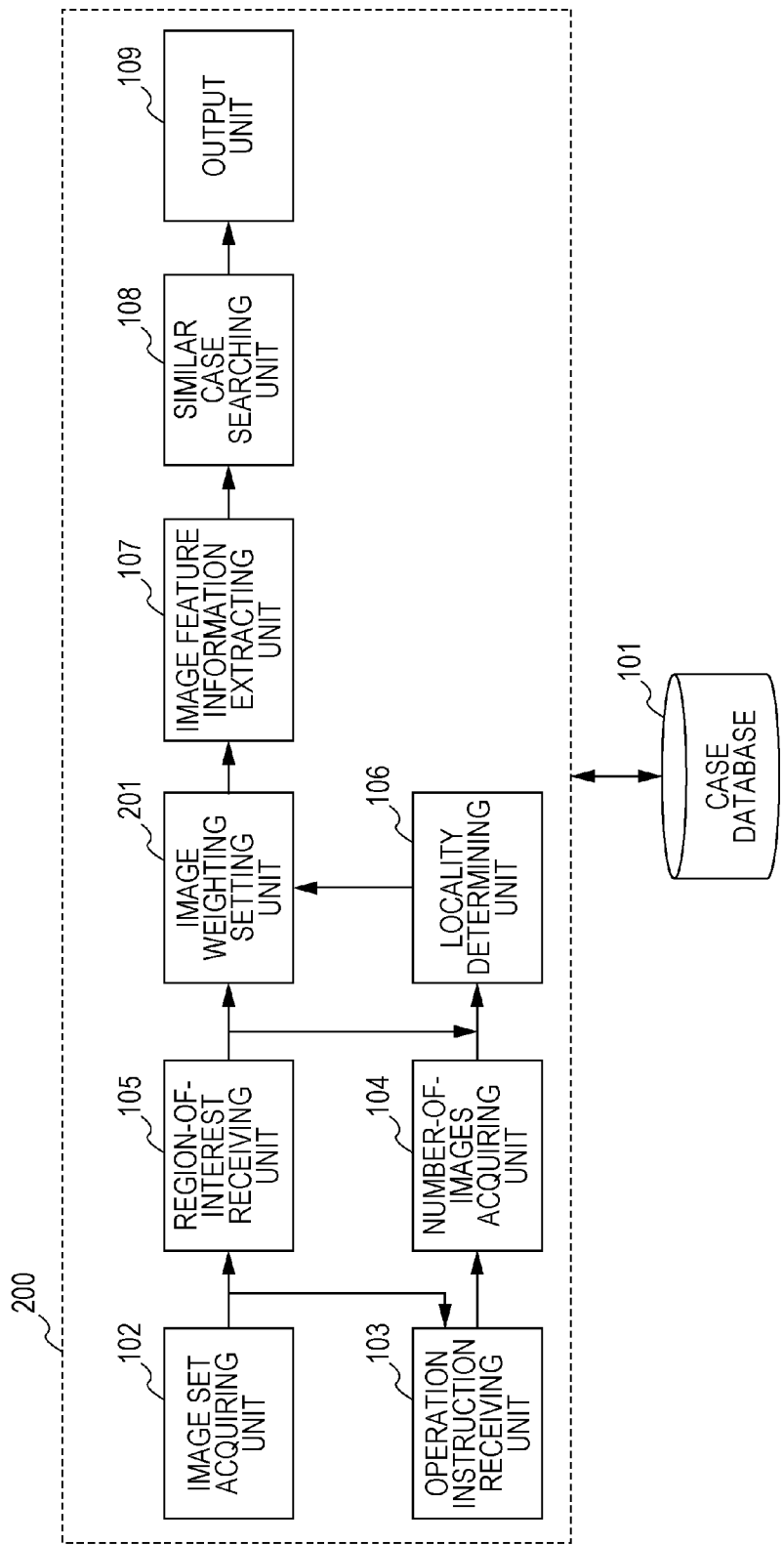
FIG. 12 is a block diagram illustrating a functional configuration of a similar case searching apparatus in accordance with a second exemplary embodiment.

FIG. 12 is a block diagram illustrating a functional configuration of similar case searching apparatus 200 in accordance with a second exemplary embodiment. In FIG. 12, substantially the same components as those in FIG. 1 are indicated by the same reference marks, and detailed description on them will occasionally be omitted. Similar case searching apparatus 200 shown in FIG. 12 has image weighting setting unit 201 which weights an image acquired from region-of-interest receiving unit 105 according to a determination result acquired from locality determining unit 106. That is, the present exemplary embodiment has a feature of weighting an image in which a region of interest has been set according to the locality determination result.

In the first exemplary embodiment describe above, the region for extracting the image feature information is changed according to the locality determination result. Specifically, the image feature information with respect to a focal lesion is extracted from the region of interest, and the image feature information with respect to a diffuse lesion, on the other hand, is extracted from an image region including both the region of interest and a region outside the region of interest, for example, an entire area of an organ containing the region of interest. In this method, similar case search can be effectively made in a condition that adequate number of past cases are stored in case database 101, because many cases similar in the morphology of the entire lesion can be searched in this condition. However, when the number of past cases stored in case database 101 is not adequate, cases similar in only a part of a lesion would also be included in the search result with respect to a diffuse lesion, which is large in the dispersion of the lesion morphology. If a similarity in an image feature which is different from a user's intention is strongly reflected, cases contrary to the user's search intension would be searched, so that the search accuracy would be reduced. To prevent this reduction of search accuracy, it is necessary to properly reflect the lesion morphology in the region of interest to the extracted image feature information even with respect to a diffuse lesion.

Accordingly, similar case searching apparatus 200 according to the present exemplary embodiment has image weighting setting unit 201 which sets weighting for an image which is an object of the similar case search according to a determination result acquired from locality determining unit 106. Image weighting setting unit 201 weights pixel values in the image acquired from region-of-interest receiving unit 105 in such a manner that the region of interest becomes a center of weighting when the object part has been determined as a diffuse lesion by locality determining unit 106, and the pixel-value-weighted image is output to image feature information extracting unit 107. By this weighting, search of a similar case matched to a user's intention becomes possible even if an adequate number of cases are not stored in case database 101. Specific weighting method will be described later.

Figure 13:
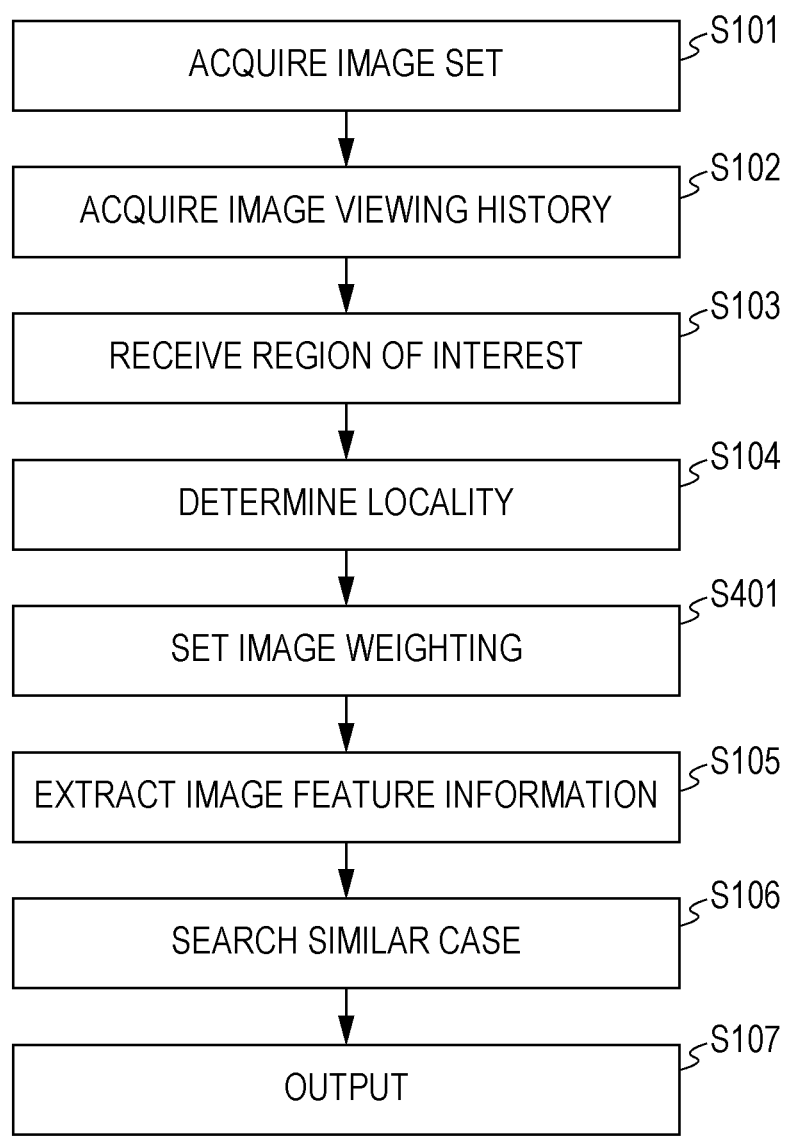
FIG. 13 is a flowchart illustrating a flow of processes performed by the similar case searching apparatus in accordance with the second exemplary embodiment.

FIG. 13 is a flowchart illustrating an overall flow of the processes performed by similar case searching apparatus 200 shown in FIG. 12. In FIG. 13, substantially the same steps as those shown in FIG. 4 are indicated by the same reference marks, and detailed description on them will occasionally be omitted.

After the locality is determined in step S104, when the object part has been determined as a diffuse lesion by locality determining unit 106, image weighting setting unit 201 weights pixel values in the image acquired from region-of-interest receiving unit 105 in such a manner that the region of interest becomes a center of weighting (step S401).

Figure 14B:
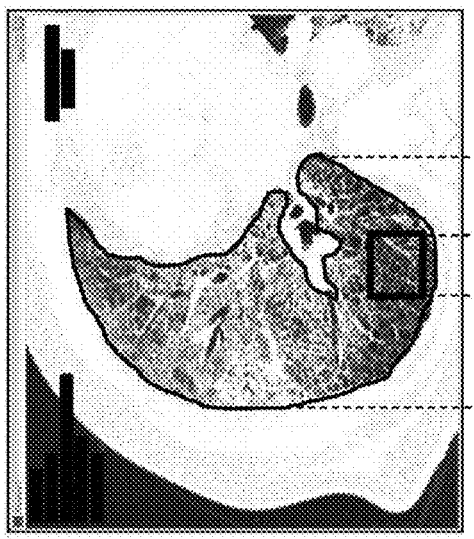
FIG. 14B is a conceptual diagram of image weighting in a case of a diffuse lesion in accordance with the second exemplary embodiment.
Figure 14B:
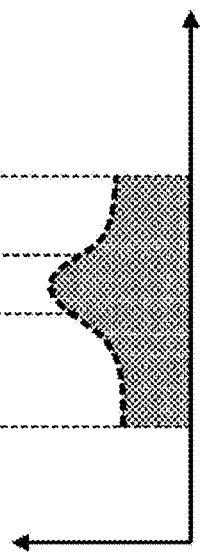
Figure 14A:
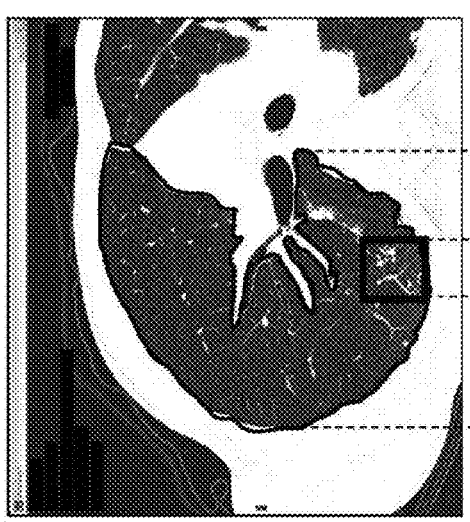
FIG. 14A is a conceptual diagram of image weighting in a case of a focal lesion in accordance with the second exemplary embodiment.
Figure 14A:
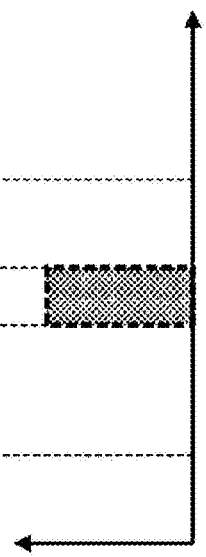

As a specific weighting method, for example, pixel values may be updated by using weighting factors having such values that become smaller with increase of the distance from the center coordinates of the region of interest. FIG. 14A is a conceptual diagram of image weighting in a case of a focal lesion, and FIG. 14B is a conceptual diagram of image weighting in a case of a diffuse lesion. In the case of the diffuse lesion, as shown in FIG. 14B, the region of interest is set as a center of weighting, and pixels are weighted non-uniformly from the region of interest, so that it is possible to search a similar case in such a condition that pixels at the center of the region of interest are enhanced and pixels outside the region of interest are also considered. As a result, even if an adequate number of past cases are not stored in case database 101, a similar case matched to a user's search intension can be searched with respect to a diffuse lesion.

As described above, according to the present exemplary embodiment, a highly accurate similar case search can be made with respect to a diffuse lesion even if the number of stored cases is small.

Incidentally, it is explained in the exemplary embodiment that the lesion determination apparatus including image set acquiring unit 102, operation instruction receiving unit 103, number-of-images acquiring unit 104, and locality determining unit 106 is used for a similar case search. However, application of the lesion determination apparatus in accordance with the present disclosure is not limited to this use. The lesion determination apparatus in accordance with the present disclosure is applicable to any uses for which a result of discrimination between a focal lesion and a diffuse lesion is useful. For example, the lesion determination apparatus in accordance with the present disclosure can also be used for a comparative interpretation system, which measures the size of a lesion automatically when the lesion is a focal lesion.

Figure 15:
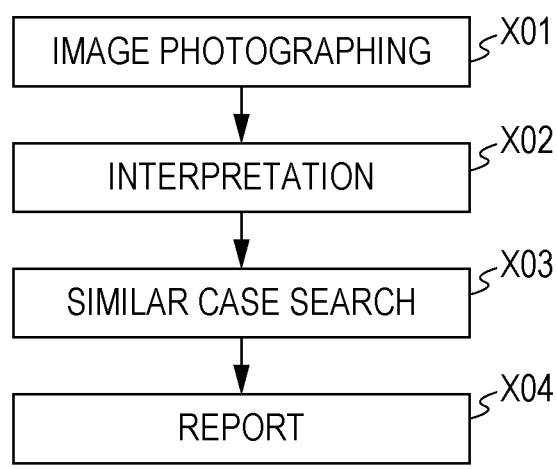
FIG. 15 is a flowchart for showing a position of the similar case search.

Here, supplemental explanation about the similar case search will be made. FIG. 15 is a flowchart for showing a position of the similar case search in accordance with the present disclosure. As shown in FIG. 15, images such as CT images of a patient are photographed first (X01), and then an image interpreter interprets an image case from the photographed images (X02). Then, the image interpreter searches similar cases with respect to the interpreted case as necessary (X03), and writes a report by reference to the searched similar cases (X04). Here, the similar case search in accordance with the present disclosure corresponds to step X03. That is, the similar case search related to the present disclosure does not fall under the so-called medical activity, that is, a process of surgical, curative or diagnostic treatment of human beings, but is equivalent to a kind of information search technique. Accordingly, the contents of the present disclosure fall under the industrially applicable inventions.

The lesion determination apparatus and the similar case searching apparatus in accordance with the present disclosure have been described in the above based on the exemplary embodiments. However, the present disclosure should not be limited to the exemplary embodiments. For example, various modifications which any person skilled in the art may think of and apply to the present exemplary embodiments, and other embodiments which may be made by combining components of different exemplary embodiments should be included within a scope of the present disclosure without departing from the spirit of the present disclosure.

Each of the lesion determination apparatus and similar case searching apparatus may be implemented as, specifically, a computer system including a microprocessor, a read-only memory (ROM), a random access memory (RAM), a hard disk drive, a display unit, a keyboard, a mouse, and the like. A computer program is stored in the RAM or the hard disk drive. The microprocessor operating according to the computer program allows the lesion determination apparatus and the similar case searching apparatus to achieve their functions. Here, the computer program is configured by combining a plurality of instruction codes indicating instructions for the computer so as to allow execution of predetermined functions.

Further, a part or all of the components configuring the lesion determination apparatus and the similar case searching apparatus may be implemented as a large scale integrated circuit known as a system LSI (Large Scale Integration). The system LSI is an ultra multi-function LSI produced by integrating a plurality of construction parts on a single chip, and specifically a computer system configured to include components such as a microprocessor, a ROM, and a RAM. A computer program is stored in the RAM. The microprocessor operating according to the computer program allows the system LSI to achieve its functions.

Furthermore, a part or all of the components configuring the lesion determination apparatus and the similar case searching apparatus may be implemented as an IC card which can be detachably attached to the similar case searching apparatus or monolithic module. The IC card or the module is a computer system including a microprocessor, a ROM, a RAM, and the like. The IC card or the module may include the ultra multi-function LSI. The microprocessor operating according to a computer program allows the IC card or the module to achieve its functions. The IC card or the module may also be implemented to be tamper resistant.

Further, the present disclosure may be regarded as the methods. Furthermore, the present disclosure may be regarded as a computer program for causing a computer to execute the methods, or as a digital signal including the computer program.

Further, the present disclosure may be regarded as a form in which the computer program or digital signal is recorded in a non-transitory, computer-readable storage medium such as a flexible disk, a hard disk, a CD-ROM, an MO, a DVD, a DVD-ROM, a DVD-RAM, a BD (Blu-ray Disc (registered trademark)), and other semiconductor memories. Furthermore, the present disclosure may be regarded as the digital signal recorded in the non-transitory storage medium.

Further, the present disclosure may be regarded as a form in which the computer program or digital signal is transmitted through an electrical communications line, a wireless or wired communications line, a network represented by the internet, data broadcasting, or the like.

Further, the present disclosure may be regarded as a computer system including a microprocessor and a memory such that the memory stores the computer program and the microprocessor operates according to the computer program.

Further, the present disclosure may be regarded as another independent computer system by transferring the program or digital signal recorded in the non-transitory recording medium or by transferring the program or digital signal through the network and the like.

INDUSTRIAL APPLICABILITY

The present disclosure is applicable to a similar case searching apparatus or the like for outputting a similar case with respect a result of a diagnosis made by an image interpreter.

What is claimed is:

1. A lesion determination apparatus comprising:
   an image set acquiring unit configured to acquire a tomography image set containing a plurality of tomography images of an object part;
   an operation instruction receiving unit configured to receive a first operation instruction to view tomography images included in the plurality of tomography images in a first order in which a tomography image position number for identifying each of the tomography images increases, and a second operation instruction to view tomography images included in the plurality of tomography images in a second order in which the tomography image position number decreases;
   a number-of-images acquiring unit configured to acquire and record, on occurrence of a direction change that is either a first state in which the second operation instruction is received immediately after receipt of the first operation instruction or a second state in which the first operation instruction is received immediately after receipt of the second operation instruction, a number of one-directionally viewed images that is either a number of tomography images continuously viewed in response to continuous first operation instructions including the first operation instruction contained in the first state or a number of tomography images continuously viewed in response to continuous second operation instructions including the second operation instruction contained in the second state; and
   a locality determining unit configured to determine whether the object part is a focal lesion or a diffuse lesion based on a change in the number of one-directionally viewed images,
   wherein the tomography image position number is assigned such that a tomography image of a tomographic slice plane closer to a particular portion of the object part has a smaller tomography image position number.

2. The lesion determination apparatus according to claim 1, wherein the locality determining unit determines that the object part is a focal lesion when the number of one-directionally viewed images has monotonically decreased with occurrence of the direction change, and otherwise determines that the object part is a diffuse lesion.

3. The lesion determination apparatus according to claim 2, wherein the locality determining unit excludes the number of one-directionally viewed images from consideration for determination when the number of one-directionally viewed images is equal to or smaller than a predetermined number.

4. The lesion determination apparatus according to claim 1, wherein the locality determining unit sets, as a predetermined threshold value, the number of one-directionally viewed images at a third direction change counted from a start of displaying the tomography image set, and determines that the object part is a focal lesion when the number of one-directionally viewed images at each of a fourth and subsequent direction changes is equal to or smaller than the predetermined threshold value, and otherwise determines that the object part is a diffuse lesion.

5. The lesion determination apparatus according to claim 1, wherein when a new direction change has occurred again within a predetermined period of time from a previous direction change, the number-of-images acquiring unit determines that the new direction change and the previous direction change did not occur.

6. A similar case searching apparatus for searching a similar case from a case database in which a plurality of case data items containing medical images have been registered, the similar case searching apparatus comprising:
   the lesion determination apparatus according to claim 1;
   a region-of-interest receiving unit configured to receive a setting of a region of interest with respect to tomography images;
   an image feature information extracting unit configured to extract image feature information from the region of interest when the locality determining unit determines that the object part is a focal lesion, and configured to extract image feature information from an image region including both the region of interest and a region outside the region of interest when the locality determining unit determines that the object part is a diffuse lesion; and
   a similar case searching unit configured to search a similar case data item from the case database by comparing the image feature information extracted by the image feature information extracting unit to image feature information extracted from medical images contained in case data items registered in the case database.

7. The similar case searching apparatus according to claim 6, wherein the image feature information extracting unit extracts image feature information from an entire region of an organ including the region of interest when the locality determining unit determines that the object part is a diffuse lesion.

8. The similar case searching apparatus according to claim 6, wherein the region-of-interest receiving unit receives the setting of the region of interest only when the locality determining unit determines that the object part is a focal lesion.

9. The similar case searching apparatus according to claim 6, further comprising an image weight setting unit configured to weight pixel values of the image in which the region of interest has been set in such a manner that the region of interest becomes a center of weighting when the locality determining unit determines that the object part is a diffuse lesion.

10. The similar case searching apparatus according to claim 6, further comprising an output unit configured to output the case data item obtained by the similar case searching unit to outside.

11. A lesion determination method comprising the steps of:
    acquiring a tomography image set containing a plurality of tomography images of an object part;

receiving a first operation instruction to view tomography images included in the plurality of tomography images in a first order in which a tomography image position number for identifying each of the tomography images increases, and a second operation instruction to view tomography images included in the plurality of tomography images in a second order in which the tomography image position number decreases;

acquiring and recording, on occurrence of a direction change that is either a first state in which the second operation instruction is received immediately after receipt of the first operation instruction or a second state in which the first operation instruction is received immediately after receipt of the second operation instruction, a number of one-directionally viewed images that is either a number of tomography images continuously viewed in response to continuous first operation instructions including the first operation instruction contained in the first state or a number of tomography images continuously viewed in response to continuous second operation instructions including the second operation instruction contained in the second state; and determining whether the object part is a focal lesion or a diffuse lesion based on a change in the number of one-directionally viewed images, wherein the tomography image position number is assigned such that a tomography image of a tomographic slice plane closer to a particular portion of the object part has a smaller tomography image position number.

12. A similar case searching method for searching a similar case by a computer from a case database in which a plurality of case data items containing medical images have been registered, the method comprising:

performing the lesion determination method according to claim 11;

receiving a setting of a region of interest with respect to the tomography images;

extracting image feature information from the region of interest when it is determined by the lesion determination method that the object part is a focal lesion, and extracting image feature information from an image region including both the region of interest and a region outside the region of interest when it is determined by the lesion determination method that the object part is a diffuse lesion; and searching a similar case data item from the case database by comparing the extracted image feature information to image feature information extracted from medical images contained in case data items registered in the case database.

13. A non-transitory computer-readable storage medium having stored therein a program for causing a computer to execute the similar case searching method according to claim 12.

14. A non-transitory computer-readable storage medium having stored therein a program for causing a computer to execute the lesion determination method according to claim 11.

15. A lesion determination apparatus comprising:

an operation instruction receiving unit configured to receive an operation instruction to view a plurality of tomography images having a common normal direction sequentially in a predetermined direction, and an operation instruction to view the plurality of tomography images sequentially in an opposite direction to the predetermined direction; and a locality determining unit configured to determine, on occurrence of a direction change in which a viewing direction is changed according an operation instruction received by the operation instruction receiving unit, that an object part is a focal lesion when a number of one-directionally viewed images has monotonically decreased, and is a diffuse lesion when the number of one-directionally viewed images has not monotonically decreased, the number of one-directionally viewed images being a number of images of the tomography images having been viewed continuously in an identical direction until the occurrence of the direction change.

16. A similar case searching apparatus for searching a similar case from a case database in which a plurality of case data items containing medical images have been registered, the similar case searching apparatus comprising:

the lesion determination apparatus according to claim 15;

a region-of-interest receiving unit configured to receive a setting of a region of interest with respect to the tomography images;

an image feature information extracting unit configured to extract image feature information from the region of interest when the locality determining unit determines that the object part is a focal lesion, and configured to extract image feature information from an image region including both the region of interest and a region outside the region of interest when the locality determining unit determines that the object part is a diffuse lesion; and a similar case searching unit configured to search a similar case data item from the case database by comparing the image feature information extracted by the image feature information extracting unit to image feature information extracted from medical images contained in case data items registered in the case database.

17. The similar case searching apparatus according to claim 16, wherein the region-of-interest receiving unit receives the setting of the region of interest only when the locality determining unit determines that the object part is a focal lesion.

\* \* \* \* \*